United States Patent [19]

Cook et al.

[11] Patent Number: 5,069,902

[45] Date of Patent: Dec. 3, 1991

[54] VIRUS AND VACCINE THEREFROM FOR USE AGAINST TURKEY RHINOTRACHEITIS

[75] Inventors: Jane K. A. Cook, Huntingdon; Christine A. Dolby, Chalfont St. Peter; Albert P. A. Mockett, Huntingdon; Matthew M. Binns, Huntingdon; Judith A. Frazier, Huntingdon; Philip Box, Watlington, all of England

[73] Assignee: British Poultry Federation Research Association, London, England

[21] Appl. No.: 195,600

[22] Filed: May 18, 1988

[30] Foreign Application Priority Data

May 21, 1987 [GB] United Kingdom ............... 87/12042
Aug. 28, 1987 [GB] United Kingdom ............... 87/20318

[51] Int. Cl.$^5$ ........................ A61K 39/12; C12N 7/00
[52] U.S. Cl. ........................................ 424/89; 424/88; 435/235.1; 435/236; 435/237
[58] Field of Search ..................... 424/89, 88; 435/235, 435/236, 237

[56] References Cited

U.S. PATENT DOCUMENTS

| | | | |
|---|---|---|---|
| 4,122,167 | 10/1978 | Buynak et al. | 424/89 |
| 4,145,252 | 3/1979 | Buynak et al. | 424/89 |
| 4,810,493 | 3/1989 | Patrick et al. | 424/89 |

FOREIGN PATENT DOCUMENTS 1560185 1/1980 United Kingdom.

OTHER PUBLICATIONS

McDougal and Cook, *Veterinary Record*, Issue 118, pp. 206–207, 1986.

*Primary Examiner*—Garnette D. Draper
*Assistant Examiner*—Abdel A. Mohamed
*Attorney, Agent, or Firm*—Nixon & Vanderhye

[57] ABSTRACT

A virus and a vaccine therefrom for use against diseases in fowl caused by turkey rhinotracheitis or serologically related strains. The virus is an attenuated strain of the virus of contagious turkey rhinotracheitis. Turkeys may be vaccinated to stop them getting turkey rhinotracheitis, and chickens may be vaccinated to stop them getting swollen head syndrome.

11 Claims, 2 Drawing Sheets

FIG.1a     FIG.1b
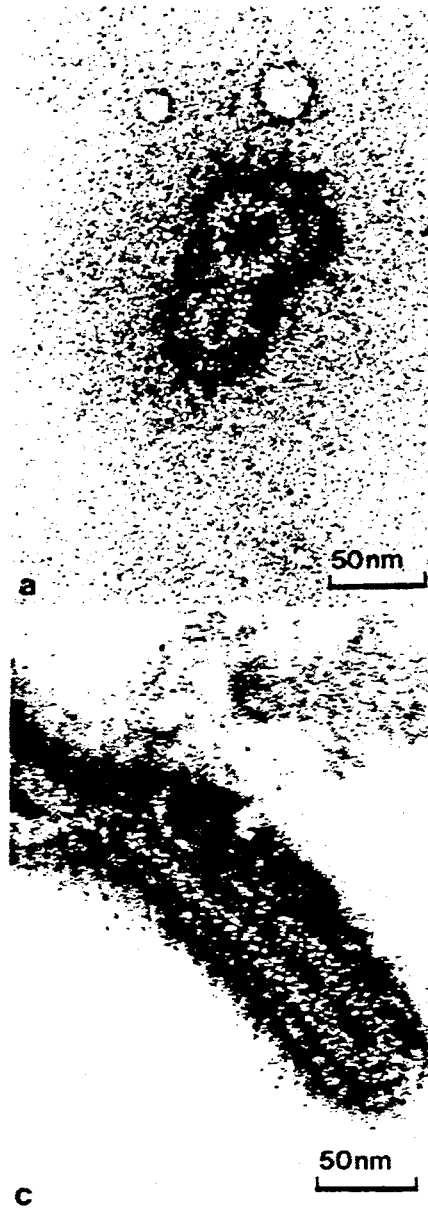
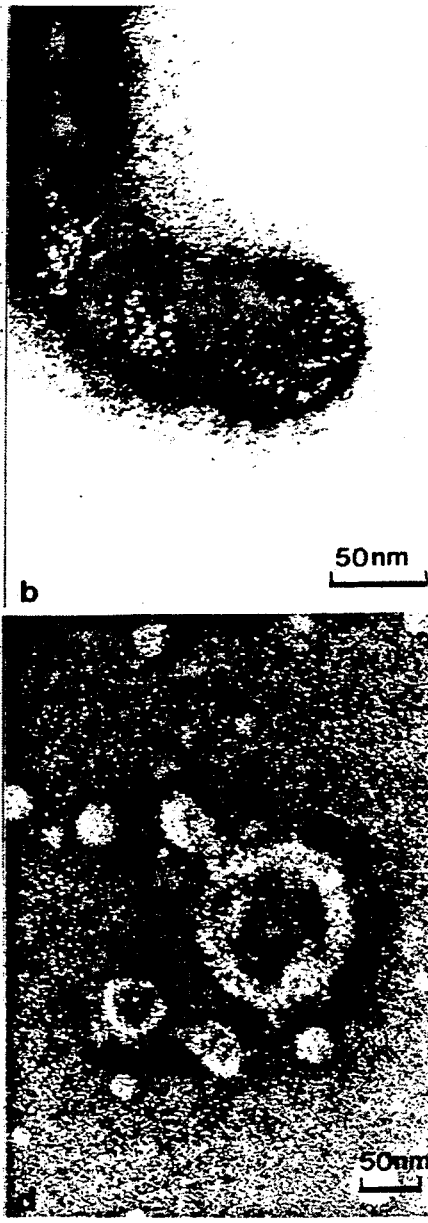
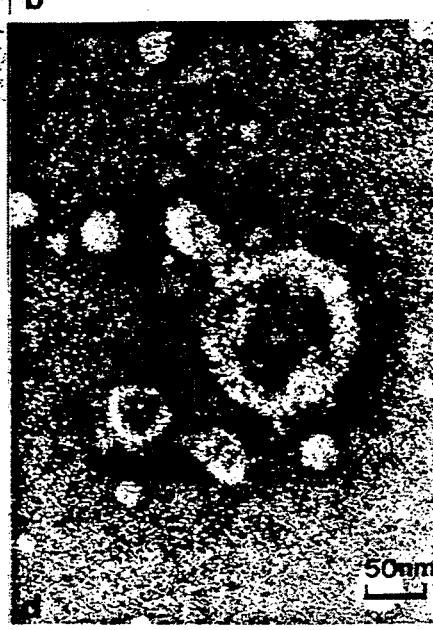
FIG.1c     FIG.1d

FIG.2a  FIG.2b
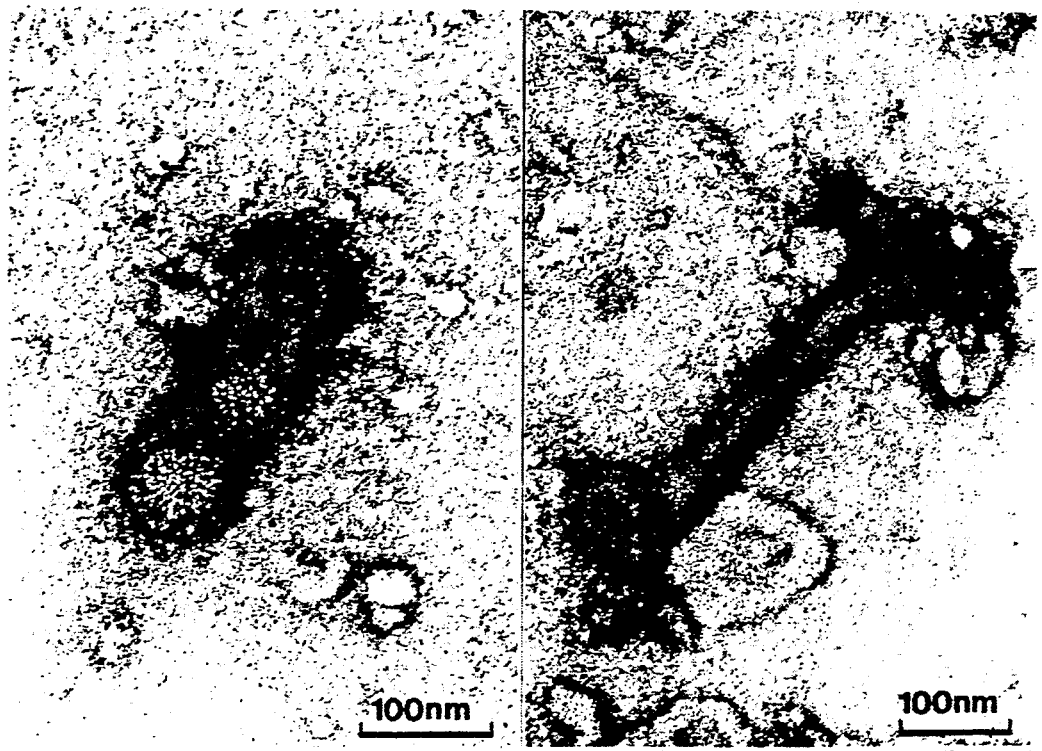
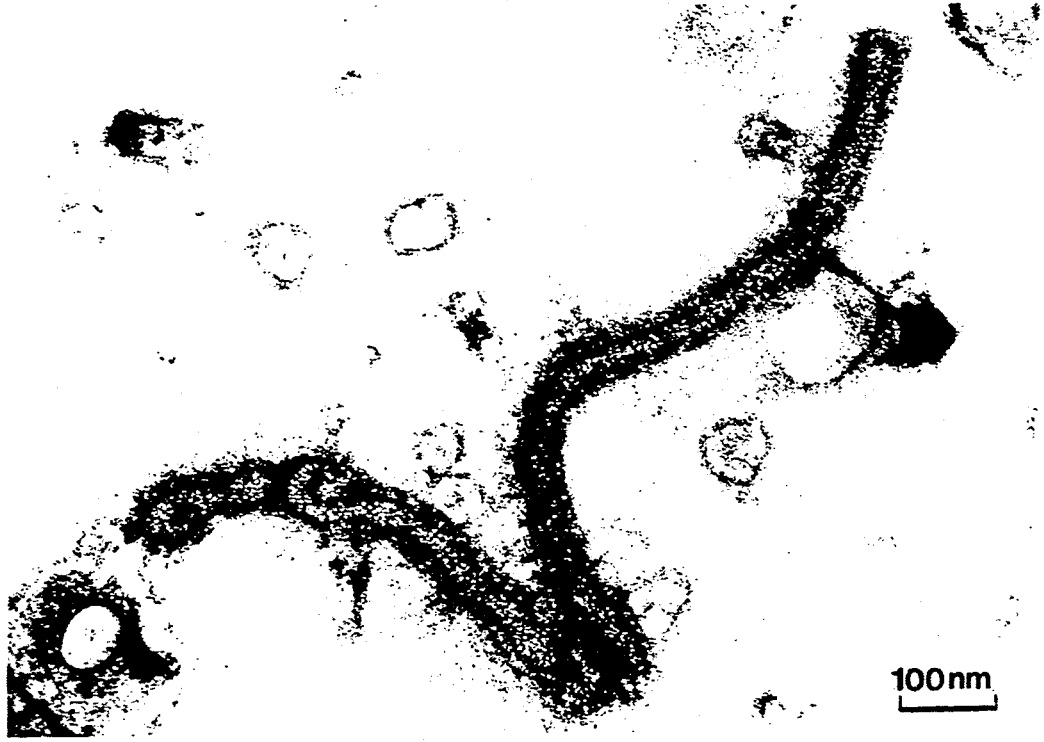
FIG.2c

VIRUS AND VACCINE THEREFROM FOR USE AGAINST TURKEY RHINOTRACHEITIS

This invention relates to an attenuated virus and a vaccine therefrom for use against diseases in fowl caused by turkey rhinotracheitis virus or serologically related strains.

The commercial rearing of fowl such as for example turkeys and chickens is well known and it is effected on a large scale. Turkeys are no longer eaten substantially solely at Christmas time and they are also no longer eaten just in the form of the cooked whole bird. For example, modern turkey growing methods, modern apparatus and extensive publicity campaigns have resulted in turkeys being eaten throughout the year as cooked whole birds, cooked bird portions, and as turkey meat in the form of turkey rolls and turkey burgers.

With the advent of the commercial rearing of turkeys, there has arisen a respiratory disease of turkeys which has been called turkey rhinotracheitis. The turkey rhinotracheitis first occurred in Great Britain in June 1985 but a clinically similar disease was known abroad for some years before this date. Turkey rhinotracheitis is an acute and highly contagious respiratory disease which can affect turkeys of any age. Morbidity and mortality rates can be as high as 100 per cent and 50 per cent respectively, and this is obviously very damaging to the turkey growing economy.

Turkey rhinotracheitis is extremely difficult to treat. The initial infecting virus rapidly de-ciliates the trachea of the turkeys. Initial infection with turkey rhinotracheitis virus is often followed by infection with a variety of bacteria which do not normally cause mortality on their own. Normal methods of treatment often prove to be ineffective. This results in those turkeys that survive the infection of the initial infecting virus having a chronic infection. These turkeys are unthrifty and grow poorly. Normal drug treatments have little effect on the bacteria once they are established in the respiratory system and, furthermore, there is no drug treatment for the initial infecting virus.

In addition to attacking turkeys, the turkey rhinotracheitis virus or serologically related strains also apparently attack other fowl such for example as chickens, guinea fowl, pheasants and ducks. Chickens may be affected irrespective of whether they are commercially reared as broilers for eating or as layers for egg laying. The disease symptoms in these other fowl when invaded by the turkey rhinotracheitis virus or serologically related strains may be the same as or different from the disease symptoms that occur in turkeys. Infected chickens are often referred to as having "swollen head syndrome" and such chickens may have swelling of the peri and infraorbital sinuses together with opisthotonos and torticollis. Also, the chickens may lose their ability to move in a coordinated manner.

It is an aim of the present invention to reduce the above mentioned problems caused by the turkey rhinotracheitis virus or the serologically related strains.

BRIEF DESCRIPTION OF THE DRAWINGS

FIGS. 1a, 1b, 1c and 1d are electron micrographs of the parent-known strain of turkey rhinotracheitis virus showing many spherical particles.

FIGS. 2a, 2b and 2c are electron micrographs of the novel attenuated strain of turkey rhinotracheitis virus.

Accordingly, this invention provides an attenuated strain of the virus of contagious turkey rhinotracheitis, wherein said attenuated strain is produced by alternate embryonic egg and tracheal organ culture passaging of the virus of contagious turkey rhinotracheitis.

The alternate embryonic egg and tracheal organ culture passaging may be effected from 20-40 times, and is presently preferably effected 30 times.

The alternate embryonic egg and tracheal organ culture passaging preferably uses avian eggs and avian tracheal organ cultures, with embryonic eggs and tracheal organ cultures from chickens being presently especially preferred. The passaging may be carried out in other cell or organ culture systems.

The present invention also provides an attenuated strain of the virus of contagious turkey rhinotracheitis, wherein said attenuated strain is deposited under deposit Ser. No. V87051102 at the culture collection specified herein.

The culture collection is the European Collection of Animal Cell Cultures, at the PHLS Centre For Applied Microbiology & Research, Porton Down, Salisbury, Wiltshire, England. The attenuated strain of the virus of contagious turkey rhinotracheitis deposited on May 11, 1987, under deposit Ser. No. V87051102 was produced by the above mentioned alternate embryonic egg and tracheal organ culture passaging.

As will be explained in more detail hereinbelow, the attenuated strain of the virus of contagious turkey rhinotracheitis can be used to form a vaccine for treating fowl to control the primary viral infection due to the turkey rhinotracheitis virus or serologically related strains. The secondary bacterial infections which cause most of the mortality and all the poor performance subsequent to the infection, are all normal pathogens of fowl and, in the absence of the turkey rhinotracheitis virus or serologically related strains, they cause no problems which cannot easily be treated with available drug therapy. Thus, by controlling the primary viral infection, the above morbidity and mortality rates can be considerably reduced with a consequent improvement, for example in turkey growing performance and in chicken rearing and egg laying, all of which are urgently required.

The attenuated strain of the virus of contagious turkey rhinotracheitis which is deposited under deposit Ser. No. V87051102 at the culture collection specified herein is a novel attenuated strain which is different from other strains of the virus found by research workers in the field, such for example as disclosed by McDougall and Cook in the Veterinary Record (1986), Issue 118, at pages 206-207. The novel attenuated strain is able to induce specific immunity for protecting against the invading turkey rhinotracheitis virus, without causing the symptoms of the disease. Similarly, the novel attenuated strain may be able to produce specific immunity antibodies for protecting against invading viruses which are serologically related to turkey rhinotracheitis virus. The novel attenuated strain is stable in that it has been found not to revert to virulence under at least twelve bird to bird passages.

The attenuated strain of the virus of contagious turkey rhinotracheitis may be one that has been obtained from a parent strain of the virus of contagious turkey rhinotracheitis, the parent strain having the following characteristics:

(a) it is pleomorphic;

(b) many particles are spherical with a diameter of 80-120 nm; elongated and bizarre forms are also found;

(c) the particles have densely packed surface projections approximately 12-14 nm in length, broadening towards the distal end;

(d) it does not agglutinate chicken, turkey, goose, mouse, guinea pig or rabbit erythrocytes at 4° C., room temperature or 37° C.;

(e) it is sensitive to treatment with chloroform;

(f) it is inactivated within 20 minutes when heated at 56° C.;

(g) it is stable over a wide pH range but it is inactivated within 30 minutes at pH 2.1;

(h) it is a ribonucleic acid (RNA) virus with a buoyant density in sucrose of approximately 1.18-1.19 g/ml; and (i) it contains at least 7 virus-specific polypeptides of approximately molecular weight 97*, 82*, 53*, 43, 40, 35 and 15* K daltons,—the ones marked with an asterisk being glycosylated.

The attenuated strain may have the following characteristics:

(a) it is neutralised by anti-serum raised against the parent strain;

(b) anti-serum raised in turkeys to the attenuated strain neutralises the parent strain; and (c) it has a similar protein profile to the parent strain.

The parent strain is a known strain which is referred to by McDougall and Cook in the above mentioned article in the Veterinary Record. The analysis of the viral mRNAs and polypeptides induced by the turkey rhinotracheitis virus, along with its other characteristics (a) to (i) above suggest that the virus is a member of the Paramyxoviridae family and has some features in common with respiratory syncytial virus, a member of the pneumovirus genus.

The attenuated strain of the virus of contagious turkey rhinotracheitis may be one that has an electron micrograph as shown in FIG. 2 of the accompanying drawings to be described hereinbelow.

The present invention further provides a live virus cultural vaccine for use against diseases in fowl caused by turkey rhinotracheitis virus or serologically related strains, wherein said vaccine comprises an attenuated strain of the virus of contagious turkey rhinotracheitis as described above.

The live virus cultural vaccine may be for use against turkey rhinotracheitis in turkeys. The live virus cultural vaccine may also be for use against swollen head syndrome in chickens. The live virus cultural vaccine may also be for use against conditions caused by turkey rhinotracheitis virus or serologically related strains in fowl other than turkeys and chickens.

The live virus cultural vaccine may be one in which the vaccine contains tracheal organ culture fluid or allantoic cavity fluid as a liquid carrier for the attenuated strain of the virus of contagious turkey rhinotracheitis.

The invention still further provides a method of preparing an attenuated strain of the virus of contagious turkey rhinotracheitis, wherein said method comprises attenuating a parent strain of the virus of contagious turkey rhinotracheitis by alternate embryonic egg and tracheal organ culture passaging.

In the method of the invention, the alternate embryonic egg and tracheal organ culture passaging may be effected from 20-40 times, and preferably 30 times. The alternate embryonic egg and tracheal organ culture passaging preferably uses embryonic eggs and tracheal organ cultures from chickens.

The method of the invention may include the step of freeze drying the prepared attenuated strain of contagious turkey rhinotracheitis.

The invention further provides a method of preparing a live virus cultural vaccine, wherein said method comprises producing an attenuated strain of the virus of contagious turkey rhinotracheitis by the said method of the invention.

The method of preparing the live virus cultural vaccine may include the step of reconstituting a freeze dried form of the prepared attenuated strain of the virus of contagious turkey rhinotracheitis.

The method of preparing the live virus cultural vaccine may also include the step of growing the attenuated strain of the virus of contagious turkey rhinotracheitis by repeated inoculation and harvesting. The growing may be effected in tracheal organ culture fluid or in allantoic cavity fluid.

During the preparation of the vaccine, the attenuated strain of the virus of contagious turkey rhinotracheitis may be purified in any desired way such for example as by gel filtration, separation, gradient centrifuging, and adsorption and subsequent elution. The vaccine may be concentrated using, for example, zonal centrifuging, molecular filtration, or adsorption and subsequent elution. The vaccine may be stabilised by the addition of stabilisers and made storable by the addition of suitable preservatives such for example as bovine serum albumen or gelatin.

The produced vaccine may be subjected to checks for sterility, harmlessness and immunogenic activity.

For a better understanding of the present invention, some specific Examples are given hereinbelow, the Examples being given by way of illustration only.

EXAMPLE 1

Attenuation of Turkey Rhinotracheitis (TRT) Virus by Alternate Chick Embryo and Tracheal Organ Culture Passaging Organ culture propagated virus was inoculated via the allantoic cavity into 9 days old chicken embryos.

Allantoic fluid was harvested 4 days later and inoculated into tracheal organ cultures. Organ culture fluid was harvested 3 days later and inoculated into 9 day old embryos via the allantoic cavity.

After alternate passaging in embryos and organ cultures for 25 times, one in vivo experiment was performed to demonstrate evidence of attenuation. Two groups of 8×4-week-old turkeys were inoculated intra-nasally with either the parent or derived strain. Twenty one days later both groups were bled and challenged intra-nasally with the parent strain. The results are given in Table 1 hereinbelow.

TABLE 1

| Inoculum | Nasal discharge (days post (challenge) 4 5 6 7 | TRT neutralising antibody titre 21 days later (reciprocal) | Clinical respiratory disease following challenge with parent strain |
|---|---|---|---|
| Parent strain | *5/8 7/8 8/8 7/8 | 56;56;56;69 83;95;125;166 mean = 88 | None |
| Derived strain | 0/8 0/8 0/8 0/8 | 17;17;38;42 56;56;56;74 | None |

TABLE 1-continued

| Inoculum | Nasal discharge (days post (challenge)) 4 5 6 7 | TRT neutralising antibody titre 21 days later (reciprocal) | Clinical respiratory disease following challenge with parent strain |
|---|---|---|---|
| (EP25) | | mean = 45 | |

*No. of turkeys showing nasal discharge/number in group

EXAMPLE 2

Characterisation of the Parent Strain of Turkey Rhinotracheitis Virus, which Parent Strain is Known From McDougall and Cook, the Veterinary Record (1986), Issue 118, Pages 206-207

The virus has been found to be pleomorphic. Many particles are spherical with a diameter of 80-120 nm. However, many larger particles are seen, and elongated and bizarre forms are also found. Virus particles have densely packed surface projections approximately 12 nm in length broadening towards the distal end. This is shown by the four electron micrographs shown in FIG. 1 under (a), (b), (c) and (d).

The virus did not agglutinate chicken, turkey, goose, mouse, guinea pig or rabbit erythrocytes at 4° C., room temperature or 37° C.

The virus was sensitive to treatment with chloroform. This virus was inactivated within 20 minutes when heated at 56° C. The virus was stable over a wide pH range but inactivated within 30 minutes at pH 2.1.

The virus is an RNA virus with buoyant density in sucrose of 1.18-1.19 g/ml. The virus contains at least 7 virus-specific polypeptides of approximate molecular weight 97*, 82*, 53*, 43, 40, 35 and 15* K daltons,—the ones marked with an asterisk being glycosylated.

EXAMPLE 3

Relationship of the Attenuated Strain to the Parent Strain

The attenuated strain was neutralised by antiserum raised against the parent strain.

Antiserum produced in turkeys against the attenuated strain neutralised the parent virus.

Parent and derived viruses were found to have similar protein profiles.

FIG. 2 shows an electron micrograph of the attenuated strain.

EXAMPLE 4

Virus Assay

Strain 3B of turkey rhinotracheitis virus was obtained and its was assayed in Eagle's Minimal Essential Medium (MEM) without serum and containing sodium bicarbonate (880 mg/l). The medium has a pH of 6.8 and the assay was conducted at a temperature of 37° C. Sealed tubes were employed. The assay demonstrated ciliostasis in chicken embryo tracheal organ culture.

EXAMPLE 5

Demonstration of the Attentuation of the Egg/Organ Culture Passaged Strain of TRT Virus The attenuated strain of TRT virus and two virulent strains were administered by eye drops to groups of 15 seven-day-old TRT-free turkey poults which were observed daily for clinical signs of infection, these being scored according to severity as shown in Table 2 hereinbelow. Virus re-isolation from nasal swabs were attempted four days after inoculation and 5 poults per group were killed five days after inoculation so that their tracheas could be examined for ciliary activity. This involved carefully preparing 10 thin slices from each trachea and examining these microscopically, coded, for ciliary activity. Activity was scored on a scale from 0 (100% ciliary activity) to 4 (total cessation of activity). Twenty one days after inoculation, all poults were bled and their sera examined for TRT antibodies by Enzyme Linked Immuno sorbant Assay (ELISA). These poults, together with a previously uninoculated group, were challenged by eye drops with a virulent strain of virus and observed daily for clinical signs of infection. Virus re-isolation was attempted four and six days after challenge and all poults were bled and killed fourteen days after challenge.

Results

The attenuated strain caused a much milder clinical disease than did either of the virulent strains, see Table 3, and the degree of tracheal damage it caused was much milder than that caused by either virulent strain, see Table 4. TRT virus was recovered from nasal swabs taken four days post inoculation from poults in all inoculated groups. Poults given the attenuated strain showed a lower serological response, as measured by ELISA, than did those which had received virulent virus, see Table 5, but were nonetheless resistant to challenge with virulent virus, see Table 3. Following challenge, the virus could be recovered from nasal swabs taken from the "challenge control" group, but not from the "vaccinated" group.

The results in this Example provide further evidence that the strain is attenuated, yet still capable of protecting poults against challenge with virulent virus.

The strain attenuated by alternate egg/organ culture passages was selected as the most suitable for use as a potential vaccine strain.

TABLE 2

| LESION SCORING SYSTEM |
|---|
| 1. Exudate when nares pressed and/or slight snicking |
| 2. Nasal discharge |
| 3. Watery eye |
| 5. Swollen sinus and/or frothy eye |
| 7. Gasping or deeply seated gurgling |
| 10. Poult looking ill |

TABLE 3

Clinical disease observed in seven day 110 TRT-free turkey poults inoculated with attenuated or virulent TRT virus and challenged twenty-one days later with virulent virus

| | Mean lesion score/bird following inoculation with - | | | |
|---|---|---|---|---|
| Days post inoculation | Attenuated strain Egg/organ culture | Virulent strain A | B | Uninoculated |
| 1 | 0 | 0 | 0 | |
| 3 | 0 | 0.4 | 1.3 | |
| 4 | 0.5 | 1.8 | 1.6 | |
| 5 | 1.2 | 2.9 | 2.7 | |
| 6 | 2.0 | 2.8 | 3.8 | |
| 7 | 1.7 | 4.9 | 3.6 | |
| 8 | 0.6 | 3.2 | 0.3 | |
| 11 | 0 | 0.5 | 0 | |
| 14 | 0 0 | 0 | | |
| 21 | 0 | 0 | 0 | |
| Total | 6.0 | 16.5 | 13.3 | |
| | Challenged | Killed | Killed | Challenged |
| +1 | 0 | | | 0 |

TABLE 3-continued

Clinical disease observed in seven day 110 TRT-free turkey poults inoculated with attenuated or virulent TRT virus and challenged twenty-one days later with virulent virus

| | Mean lesion score/bird following inoculation with - | | | |
|---|---|---|---|---|
| Days post inoculation | Attenuated strain Egg/organ culture | Virulent strain A | B | Uninoculated |
| +3 | 0 | | | 0 |
| +4 | 0 | | | 1.2 |
| +5 | 0 | | | 3.0 |
| +6 | 0 | | | 4.0 |
| +7 | 0 | | | 4.1 |
| +8 | 0 | | | 2.2 |
| +10 | 0 | | | 0 |
| Total | | | | 14.5 |

TABLE 4

Ciliary activity in tracheas of poults killed five days after inoculation with attenuated or virulent strains of TRT virus

| | Total ciliary activity in 10 organ cultures from 5 tracheas five days after inoculation with | | | |
|---|---|---|---|---|
| Poult number | Attenuated strain Egg/organ culture | Virulent strain A | B | Uninoculated |
| 1 | 0 | 36 | 32 | 7 |
| 2 | 13 | 30 | 40 | 3 |
| 3 | 29 | 38 | 40 | 4 |
| 4 | 9 | 32 | 39 | 18 |
| 5 | 5 | 39 | 39 | 7 |
| Total | 56 | 175 | 190 | 39 |

TABLE 5

Antibody response of seven day old TRT-free turkey poults inoculated with attenuated or virulent TRT virus and challenge twenty-one days later with virulent virus

| | Mean TRT ELISA antibody titre ($log_2$) following inoculation with - | | | |
|---|---|---|---|---|
| Time | Attenuated strain Egg/organ culture | Virulent strain A | B | Uninoculated |
| 21 days post inoculation | 11.14 | 12.24 | 13.74 | <5.64 |
| 14 days post challenge | 9.94 | — | — | 10.84 |

— not examined

EXAMPLE 6

(a) Preparation of the vaccine containing a live strain of turkey rhinotracheitis virus attenuated by alternate embryonic egg and tracheal organ culture passaging The virus is isolated using chicken tracheal organ cultures and was attenuated by 30 cycles of alternate embryonic egg and tracheal organ culture passaging. The virus was purified by three passages at limiting dilution in tracheal organ cultures and was then propagated in embryonic eggs. The allantoic fluid harvested 72-120 hours after inoculation was used as vaccine.

The virus fluid may be diluted as required and mixed with stabiliser and freeze dried. Each vial may contain 100-10,000 doses. Each dose contains $10^2$-$10^4 CD_{50}$.

(b) Immunisation

One dose containing $10^2$-$10^4 CD_{50}$ of live vaccine virus was administered to three week old chicks by spray.

At three weeks post vaccination, serum samples were obtained and tested for antibodies to the turkey rhinotracheitis virus by an ELISA test. A separate group of unvaccinated controls were housed separately.

Mean ELISA titres were 8.5 $log_2$ of antibody at three weeks after administration. The controls remained negative.

These experiments clearly demonstrate that the administration of a live attenuated turkey rhinotracheitis vaccine to chickens rapidly induces an immune response, as shown by the development of specific antibodies to turkey rhinotracheitis virus. It is highly likely that such vaccinated chickens will be resistant to challenge which could otherwise result in swollen head syndrome.

It is to be appreciated that the Examples and the accompanying drawings have been given solely for the purposes of illustration. Thus, for example, other methods of attenuation not given in the Examples may be employed, such for example as cell culture passaging, the selection of temperature sensitive mutants, and the use of chemical mutagens. Whilst healthy fowl such for example as turkeys and chickens are preferably vaccinated to stop them getting turkey rhinotracheitis and swollen head syndrome respectively, diseased fowl may also be treated to bring about a higher recovery rate than would normally occur.

We claim:

1. An attenuated strain of the virus of contagious turkey rhinotracheitis, which attenuated strain is deposited under the deposit Ser. No. V87051102 at the European Collection of Animal Cell Cultures.

2. An attenuated strain of the virus of contagious turkey rhinotracheitis, which attenuated strain is deposited under the deposit Ser. No. V87051102 at the European Collection of Animal Cell Cultures, and wherein said attenuated strain is produced by alternate embryonic egg and tracheal organ culture passaging of the virus of contagious turkey rhinotracheitis.

3. An attenuated strain according to claim 2 in which the alternate embryonic egg and tracheal organ culture passaging is effected from 20-40 times.

4. An attenuated strain according to claim 2 in which the alternate embryonic egg and tracheal organ culture passaging uses embryonic eggs and tracheal organ cultures from chickens.

5. A live virus cultural vaccine for use against diseases in fowl caused by turkey rhinotracheitis virus of senologically related strains wherein said vaccine comprises an effective amount of an attenuated strain of the virus of contagious turkey rhinotracheitis as claimed in claim 1 and a pharmaceutical acceptable diluent thereof.

6. A live virus cultural vaccine according to claim 5 and which is for use against turkey rhinotracheitis in turkeys.

7. A live virus cultural vaccine according to claim 5 and which is for use against swollen head syndrome in chickens.

8. A method of preparing an attenuated strain of the virus of contagious turkey rhinotracheitis, which attenuated strain is deposited under the deposit Ser. No. V87051102 at the European Collection of Animal Cell Cultures, and which method comprises attenuating a parent strain of the virus of contagious turkey rhinotracheitis by alternate embryonic egg and tracheal organ culture passaging.

9. A method according to claim 8 in which the alternate embryonic egg and tracheal organ culture passaging is effected from 20-40 times.

10. A method according to claim 8 in which the alternate embryonic egg and tracheal organ culture passaging uses embryonic eggs and tracheal organ cultures from chickens.

11. A method of preparing a live virus cultural vaccine, wherein said method comprises producing an attenuated strain of the virus of contagious turkey rhinotracheitis by a method as claimed in claim 8.

* * * * *